United States Patent
Daly et al.

(10) Patent No.: US 9,592,190 B2
(45) Date of Patent: *Mar. 14, 2017

(54) SUNSCREEN COMPOSITIONS CONTAINING AN ULTRAVIOLET RADIATION-ABSORBING POLYESTER

(71) Applicant: JOHNSON & JOHNSON CONSUMER INC., Skillman, NJ (US)

(72) Inventors: Susan Daly, Basking Ridge, NJ (US); Rocco Vincent Burgo, Mullica Hill, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 85 days.

This patent is subject to a terminal disclaimer.

(21) Appl. No.: 14/565,909

(22) Filed: Dec. 10, 2014

(65) Prior Publication Data

US 2015/0093341 A1 Apr. 2, 2015

Related U.S. Application Data

(63) Continuation of application No. 13/710,531, filed on Dec. 11, 2012, now abandoned, which is a continuation-in-part of application No. 13/535,890, filed on Jun. 28, 2012, now abandoned.

(51) Int. Cl.
*A61K 8/85* (2006.01)
*A61Q 17/04* (2006.01)
*A61K 8/06* (2006.01)
*A61K 8/81* (2006.01)

(52) U.S. Cl.
CPC ............. *A61K 8/85* (2013.01); *A61K 8/062* (2013.01); *A61K 8/8182* (2013.01); *A61Q 17/04* (2013.01)

(58) Field of Classification Search
None
See application file for complete search history.

(56) References Cited

U.S. PATENT DOCUMENTS

| | | |
|---|---|---|
| 4,107,290 A | 8/1978 | Jacquet et al. |
| 4,322,522 A | 3/1982 | Johnson et al. |
| 4,528,311 A | 7/1985 | Beard et al. |
| 4,810,489 A | 3/1989 | Murray et al. |
| 4,839,160 A | 6/1989 | Forestier et al. |
| 4,897,259 A | 1/1990 | Murray et al. |
| 5,039,782 A | 8/1991 | Langer et al. |
| 5,138,089 A | 8/1992 | Sabatelli |
| 5,157,091 A | 10/1992 | Masataka et al. |
| 5,166,234 A | 11/1992 | Kawaguchi et al. |
| 5,219,559 A | 6/1993 | Kopolow |
| 5,250,652 A | 10/1993 | Langer et al. |
| 5,459,222 A | 10/1995 | Rodgers et al. |
| 5,487,885 A | 1/1996 | Sovak et al. |
| 5,585,090 A | 12/1996 | Yoshioka et al. |
| 5,741,924 A | 4/1998 | Sovak et al. |
| 5,843,410 A | 12/1998 | Kim et al. |
| 5,869,030 A | 2/1999 | Dumler et al. |
| 5,869,099 A | 2/1999 | Keller et al. |
| 6,001,337 A | 12/1999 | Keller et al. |
| 6,048,516 A | 4/2000 | Bringhen et al. |
| 6,123,928 A | 9/2000 | Sovak et al. |
| 6,143,850 A | 11/2000 | Keller et al. |
| 6,183,728 B1 | 2/2001 | Forestier et al. |
| 6,193,959 B1 | 2/2001 | Bernasconi et al. |
| 6,294,156 B1 | 9/2001 | Lentini et al. |
| 6,391,287 B1 | 5/2002 | Baldo et al. |
| 6,413,393 B1 | 7/2002 | Van Antwerp et al. |
| 6,471,949 B2 | 10/2002 | Candau et al. |
| 6,540,986 B2 | 4/2003 | Lukenbach et al. |
| 6,620,407 B1 | 9/2003 | Gers-Barlag et al. |
| 6,767,547 B2 | 7/2004 | Gers-Barlag et al. |
| 6,800,274 B2 | 10/2004 | Bonda et al. |
| 6,814,959 B1 | 11/2004 | Muller et al. |
| 6,867,250 B1 | 3/2005 | Gupta et al. |
| 6,869,597 B2 | 3/2005 | Arnaud |

(Continued)

FOREIGN PATENT DOCUMENTS

| EP | 407932 A | 1/1991 |
|---|---|---|
| EP | 413648 A | 2/1991 |

(Continued)

OTHER PUBLICATIONS

CAS Registry entries for (1) dimerdiol CAS No. 147853-32-5; (2) di-trimethylolpropane CAS No. 23235-61-2; (3) dimethyladipate CAS No. 627-93-0; and (4) benzenepropanoic acid, 3-(2h-benzotriazol-2-yl)-5-(1,1-dimethylethyl)-4-hydroxy-,methylester CAS No. 84268-33-7, printed 2016.*
CAS registry entries for arachidyl alcohol (and) behenyl alcohol (and) arachidyl glucoside, printed 2016.*
U.S. Appl. No. 61/665,464, filed Jun. 28, 2012, Daly et al.
U.S. Appl. No. 14/132,290, filed Dec. 18, 2013, Daly et al.
U.S. Appl. No. 61/991,732, filed May 12, 2014, Daly et al.
U.S. Appl. No. 61/665,430, filed Jun. 28, 2012, Levins et al.
U.S. Appl. No. 61/665,439, filed Jun. 28, 2012, Levins et al.
"Crodacol™ C95 Product Details" from the Croda website, 2013 http://www.croda.com/home.aspx?view=dtl&d=content&s=157&r=401&p=2578&prodID-1779.
Erberich et al., "Polyglycidols with Two Orthogonal Protective Groups: Preparation, Selective Deprotection, and Functionalization", *Macromolecules* (2007), vol. 40, pp. 3070-3079.

(Continued)

*Primary Examiner* — David J Blanchard
*Assistant Examiner* — Alissa Prosser

(57) ABSTRACT

Compositions including an oil phase substantially homogeneously distributed in a continuous water phase, the oil phase including a sunscreen agent that includes a UV-absorbing polyester in an amount effective to provide the composition with an SPF of about 10 or greater and which is the polymerization reaction product of monomers including a UV-absorbing triazole, a diester, a diol and a tetrol polyol; an alkylated polyvinylpyrrolidone; and an emulsifier selected from anionic emulsifier and/or a non-ionic emulsifier, where the composition is substantially free of a non-polymeric UV-absorbing sunscreen agent and has an SPF of less than 2 in the absence of the UV-absorbing polyester.

6 Claims, No Drawings

(56) References Cited

U.S. PATENT DOCUMENTS

| | | |
|---|---|---|
| 6,881,415 B1 | 4/2005 | Gers-Barlag et al. |
| 6,899,866 B2 | 5/2005 | Bonda |
| 6,905,674 B2 | 6/2005 | L'Alloret |
| 6,951,911 B2 | 10/2005 | Tagawa et al. |
| 6,962,692 B2 | 11/2005 | Bonda et al. |
| 6,989,151 B2 | 1/2006 | Gers-Barlag et al. |
| 7,008,618 B1 | 3/2006 | Hessefort et al. |
| 7,087,692 B2 | 8/2006 | Koshti et al. |
| 7,097,828 B2 | 8/2006 | Meyer et al. |
| 7,153,494 B2 | 12/2006 | Chodorowski-Kimmes et al. |
| 7,186,415 B1 | 3/2007 | Gers-Barlag et al. |
| 7,264,795 B2 | 9/2007 | Pflücker et al. |
| 7,427,640 B1 | 9/2008 | Katayama et al. |
| 7,465,438 B2 | 12/2008 | Schunicht et al. |
| 7,534,420 B2 | 5/2009 | Bonda et al. |
| 7,749,524 B2 | 7/2010 | Lu et al. |
| 7,850,954 B2 | 12/2010 | Leblanc et al. |
| 7,914,775 B2 | 3/2011 | Cottard et al. |
| 7,988,953 B2 | 8/2011 | Poschalko et al. |
| 7,993,680 B2 | 8/2011 | Clemente et al. |
| 8,003,132 B2 | 8/2011 | Clemente et al. |
| 8,025,868 B2 | 9/2011 | Clemente et al. |
| 2001/0038829 A1 | 11/2001 | Hasebe et al. |
| 2002/0131941 A1 | 9/2002 | Habeck et al. |
| 2003/0165553 A1 | 9/2003 | Gers-Barlag et al. |
| 2004/0022836 A1 | 2/2004 | Degen et al. |
| 2004/0057914 A1 | 3/2004 | Bonda et al. |
| 2004/0096406 A1 | 5/2004 | De Poilly |
| 2004/0126339 A1 | 7/2004 | Roszell |
| 2004/0197359 A1 | 10/2004 | Yamada et al. |
| 2004/0223925 A1 | 11/2004 | L'Alloret |
| 2004/0228814 A1 | 11/2004 | Candau et al. |
| 2005/0031660 A1 | 2/2005 | Deckner |
| 2005/0036961 A1 | 2/2005 | Hansenne et al. |
| 2005/0065251 A1 | 3/2005 | Candau et al. |
| 2005/0180933 A1 | 8/2005 | Wei et al. |
| 2006/0204457 A1 | 9/2006 | Toda et al. |
| 2007/0098653 A1 | 5/2007 | Tamasawa et al. |
| 2007/0134174 A1 | 6/2007 | Irwin et al. |
| 2008/0081025 A1 | 4/2008 | Poschalko et al. |
| 2008/0089852 A1 | 4/2008 | Hotz et al. |
| 2008/0247975 A1 | 10/2008 | Dueva-Koganov et al. |
| 2008/0311234 A1 | 12/2008 | Yoneda et al. |
| 2009/0016971 A1 | 1/2009 | Gaudry et al. |
| 2009/0041688 A1 | 2/2009 | Dueva-Koganov et al. |
| 2009/0068130 A1 | 3/2009 | Spaulding et al. |
| 2009/0185988 A1 | 7/2009 | Maleski et al. |
| 2009/0214460 A9 | 8/2009 | Luukas |
| 2009/0232859 A1 | 9/2009 | Sakuta et al. |
| 2009/0258230 A1 | 10/2009 | Schlossman et al. |
| 2009/0297462 A1 | 12/2009 | Hessefort et al. |
| 2009/0324523 A1 | 12/2009 | Clemente et al. |
| 2009/0324524 A1 | 12/2009 | Clemente et al. |
| 2010/0003202 A1 | 1/2010 | Matsumoto et al. |
| 2010/0129303 A1 | 5/2010 | Dueva-Koganov et al. |
| 2010/0189661 A1 | 7/2010 | Musa et al. |
| 2010/0226867 A1 | 9/2010 | Dueva-Koganov et al. |
| 2010/0239508 A1 | 9/2010 | Mori et al. |
| 2010/0284948 A1 | 11/2010 | Ohrmann et al. |
| 2011/0014139 A1 | 1/2011 | Viala et al. |
| 2011/0027202 A1 | 2/2011 | Candau et al. |
| 2011/0104078 A1 | 5/2011 | Burgo et al. |
| 2011/0117034 A1 | 5/2011 | Satonaka et al. |
| 2011/0195036 A1 | 8/2011 | Clemente et al. |
| 2014/0004054 A1 | 1/2014 | Daly et al. |
| 2014/0004055 A1 | 1/2014 | Daly et al. |
| 2014/0004056 A1 | 1/2014 | Daly et al. |
| 2014/0004057 A1 | 1/2014 | Daly et al. |
| 2014/0004058 A1 | 1/2014 | Daly et al. |
| 2014/0004059 A1 | 1/2014 | Daly et al. |
| 2014/0004060 A1 | 1/2014 | Levins et al. |
| 2014/0004061 A1 | 1/2014 | Levins et al. |
| 2014/0004063 A1 | 1/2014 | Daly |
| 2014/0004064 A1 | 1/2014 | Daly |

FOREIGN PATENT DOCUMENTS

| | | |
|---|---|---|
| EP | 523955 A | 1/1993 |
| EP | 601080 B | 7/1995 |
| EP | 681830 A | 11/1995 |
| EP | 1051963 A | 11/2000 |
| EP | 1291370 A | 3/2003 |
| EP | 1089986 B | 3/2005 |
| EP | 2015727 B | 1/2010 |
| EP | 2198930 A | 6/2010 |
| JP | S6099186 A | 6/1985 |
| JP | 2006-265389 A | 10/2006 |
| JP | 2009-167168 A | 7/2009 |
| WO | WO 93/22366 A | 11/1993 |
| WO | WO 93/22413 A | 11/1993 |
| WO | WO 96/03369 A | 2/1996 |
| WO | WO 01/08647 A | 2/2001 |
| WO | WO 2005/092282 A | 10/2005 |
| WO | WO 2007/081209 A | 7/2007 |
| WO | WO 2008/056678 A | 5/2008 |
| WO | WO 2009/138485 A | 11/2009 |
| WO | WO 2010/060776 A | 6/2010 |
| WO | WO 2010/115009 A | 10/2010 |
| WO | WO 2010/127987 A | 11/2010 |
| WO | WO 2011/048570 A | 4/2011 |
| WO | WO 2011/070050 A | 6/2011 |

OTHER PUBLICATIONS

Evans et al., "The Colloidal Domain: where physics, chemistry, biology, and technology meet," Wiley, 1999, p. 409-416; http://www.bre.orst.edu/Courses/Colloid%20Transport/documents/DLVOPrimer.pdf.

Fitton et al., Synthesis (1987), pp. 1140-1142.

Flick, "Cosmetics Aditives: An Industrial Guide (Passage)", Jan. 1, 1991 (XP055129531), retrieved from the Interenet: URL:http://www3.pha.nu.ac.th/e-library/Cosmetic%20Sciences/Cosmetics%20Additives%20-%20An%20Industrial%20Guide%20%281991%29.pdf [retrieved on Jul. 17, 2014].

Hanson et al., "Sunscreen Enhancement of UV-induced Reactive Oxygen Species in the Skin", *Free Radical Biology & Medicine* (2006) vol. 41, pp. 1205-1212.

Haouet et al., "Preparation Et Proprietes Des Poly®-Glycidols", *European Polymer Journal* (1983), vol. 19(12), pp. 1089-1098. (English Abstract).

Kuhn et al., "Monitoring the Kinetics of Ion-Dependent Protein Folding by Time-Resolved NMR Spectroscopy at Atomic Resolution", *Journal of the American Chemical Society* (2000), vol. 122, pp. 6169-6174.

Lee et al., "Poly(allyl Glycidyl Ether)—A Versatile and Functional Polyether Platform", *Journal of Polymer Science Part A: Polymer Chemistry* (2011), vol. 49, pp. 4498-4504.

Li et al., "Synthesis of polyethylene glycol (PEG) derivatives and PEGylated-peptide biopolymer conjugates", *Biomacromolecules*, American Chemical Society, US, vol. 4, No. 4, May 17, 2003, pp. 1055-1067 (ISSN: 1525-7797, DOI: 10.1021/BM034069L) (XP002328259).

Obermeier et al., "Poly(ethylene glycol-co-allyl glycidyl ether)s: A PEG-Based Modular Synthetic Platform for Multiple Bioconjugation", *Bioconjugate Chemistry* (2011), vol. 22, pp. 436-444.

Moore et al., "Room Temperature Polyesterification", *Macromolecules* (1990), vol. 23, Issue 1, pp. 65-70.

Rokicki et al., "Hyperbranched aliphatic polyethers obtained from environmentally benign monomer: glycerol carbonate", *Green Chemistry* (2005), vol. 7, pp. 529-539.

Sunder et al., "Controlled Synthesis of Hyperbranched Polyglycerols by Ring-Opening Multibranching Polymerization", *Macromolecules* (1999), vol. 32, pp. 4240-4246.

Taton et al., "Synthesis of chiral and racemic functional polymers from glycidol and thioglycidol", *Macromolecular Chemistry and Physics* (1994), vol. 195, pp. 139-148.

Tchao, "Trans-Epithelial Permeability of Fluorescein In Vitro as an Assay to Determine Eye Irritants", *Alternative Methods in Toxicology 6, Progress in In Vitro Toxicology* (ed. A.M. Goldberg) (1988), pp. 271-283.

(56) References Cited

OTHER PUBLICATIONS

Tokar et al., "Cationic Polymerization of Glycidol: Coexistence of the Activated Monomer and Active Chain End Mechanism", *Macromolecules* (1994), vol. 27, pp. 320-322.
International search report dated Aug. 7, 2014, for corresponding international application PCT/US2013/046313.
International search report dated Jul. 8, 2014, for corresponding international application PCT/US/2013/046316.

* cited by examiner

SUNSCREEN COMPOSITIONS CONTAINING AN ULTRAVIOLET RADIATION-ABSORBING POLYESTER

This application is a continuation of U.S. Ser. No. 13/710,531 filed Dec. 11, 2012, which is a continuation-in-part of U.S. Ser. No. 13/535,890 filed Jun. 28, 2012, the complete disclosures of which are hereby incorporated herein by reference for all purposes.

FIELD OF THE INVENTION

The present invention relates to topically-acceptable sunscreen compositions comprising UV-absorbing polyesters.

BACKGROUND OF THE INVENTION

The prolonged exposure to ultraviolet (UV) radiation, such as from the sun, can lead to the formation of light dermatoses and erythemas, as well as increase the risk of skin cancers, such as melanoma, and accelerate skin aging, such as loss of skin elasticity and wrinkling.

Numerous sunscreen compositions are commercially available with varying ability to shield the body from ultraviolet light. However, numerous challenges still exist to provide sunscreen compositions that provide strong UV radiation protection, as well as resistance to washing off with water.

The challenge of creating water resistant sunscreens is further magnified if one imposes additional constraints on the sunscreen composition. The present invention provides water-resistant, aesthetic sunscreen compositions that include a polymeric sunscreen compound (i.e., an ultraviolet radiation-absorbing polyester), and that are substantially free of non-polymeric UV-absorbing sunscreen agents.

SUMMARY OF THE INVENTION

Compositions of the present invention include a discontinuous oil phase including a sunscreen agent that includes a UV-absorbing polyester in an amount effective to provide the composition with an SPF of about 10 or greater. The oil phase is substantially homogenously distributed in a continuous water phase. The UV-absorbing polyester is the polymerization reaction product of monomers comprising a UV-absorbing triazole, a diester, a diol and a tetrol polyol. The composition includes an alkylated polyvinylpyrrolidone and an emulsifier selected from the group consisting of an anionic emulsifier and a non-ionic emulsifier. The composition is substantially free of a non-polymeric UV-absorbing sunscreen agent and has an SPF of less than 2 in the absence of the UV-Absorbing polyester.

DETAILED DESCRIPTION OF THE INVENTION

Unless defined otherwise, all technical and scientific terms used herein have the same meaning as commonly understood by one of ordinary skill in the art to which the invention belongs. As used herein, unless otherwise indicated, all hydrocarbon groups (e.g., alkyl, alkenyl) groups may be straight or branched chain groups. As used herein, unless otherwise indicated, the term "molecular weight" refers to weight average molecular weight, (Mw).

Unless defined otherwise, all concentrations refer to concentrations by weight of the composition. Also, unless specifically defined otherwise, the term "essentially free of," with respect to a class of ingredients, refers to the particular ingredient(s) being present in a concentration less than is necessary for the particular ingredient to be effective to provide the benefit or property for which it otherwise would be used, for example, about 1% or less, or about 0.5% or less.

As used herein, "UV-absorbing" refers to a material or compound, e.g. a polymeric or non-polymeric sunscreen agent or a chemical moiety, which absorbs radiation in some portion of the ultraviolet spectrum (290 nm-400 nm), such as one having an extinction coefficient of at least about 1000 $mol^{-1}$ $cm^{-1}$, for at least one wavelength within the above-defined ultraviolet spectrum. SPF values disclosed and claimed herein are determined using the in-vitro method described herein below.

UV-Absorbing Polyester

Embodiments of the invention relate to compositions including a sunscreen agent that comprises a UV-absorbing polyester. Such polyesters may be characterized as the polymerization reaction, e.g., esterification and/or transesterification, product of polyols, polyacids, polyanhydrides and/or polyesters. By "polyester," it is meant a polymer having multiple repeat units, each of the repeat units including an ester functional group, [—COO—]. As such, the UV-absorbing polyester may include one or more "polyester backbone" portions, each polyester backbone portion having one or more ester functional groups that are derived by polymerization, as described herein. As used herein, "UV-absorbing polyester" may include residual free monomer which may be present resulting from the polymerization process.

According to certain embodiments, the UV-absorbing polyester is complex. By "complex," it is meant that the UV-absorbing polyester includes terminal monofunctional compounds. The UV-absorbing polyester is fully or partially terminated (by reaction) with monofunctional acids, anhydrides, monofunctional alcohols, monofunctional epoxides and/or monofunctional esters.

According to certain embodiments, the UV-absorbing polyester is cross-linked. By "cross-linked" it is meant the UV-absorbing polyester has three or more terminal groups, each terminating a branch of the UV-absorbing polyester. Accordingly, the UV-absorbing polyester may be made using one or more polyfunctional monomers that has at least three total functional groups, for example four functional groups.

According to certain embodiments, the UV-absorbing polyester comprises a plurality of independent polyester moieties, each of which is terminated, or "capped", by a UV-absorbing moiety. UV-absorbing polyesters that may be used in compositions according to the present invention are described in United States patent application publication number US2011/0104078 A1. In particular, UV-absorbing polyesters according to Scheme 6 of the application, and as further defined herein below, are useful in compositions of the present invention that are substantially free of non-polymeric UV-absorbing sunscreen agents.

The UV-absorbing polyester is UV-absorbing in that it includes UV-absorbing moieties, as discussed herein below, and therefore absorbs radiation in some portion of the ultraviolet spectrum (290 nm-400 nm), such as one having an extinction coefficient of about 1000 $mol^{-1}$ $cm^{-1}$ or more, for example greater than 10,000 or 100,000 or 1,000,000 $mol^{-1}$ $cm^{-1}$, for at least one wavelength within the above-defined ultraviolet spectrum. The UV-absorbing moiety may absorb predominantly in the UV-A portion (320 nm to 400 nm) or predominantly in the UV-B portion (290 nm to 320 nm) of the ultraviolet spectrum. Particularly suitable examples UV-absorbing moieties include UV-absorbing triazoles. By "UV-absorbing triazole" it is meant a UV-absorbing moiety containing a five-membered heterocyclic ring with two carbon and three nitrogen atoms. Typical UV-absorbing triazoles are benzotriazoles, which include the mentioned five-membered heterocyclic ring fused with a six-membered homocyclic aromatic ring. Examples of UV-absorbing triazoles include, for example, compounds of the formula (II) or (III):

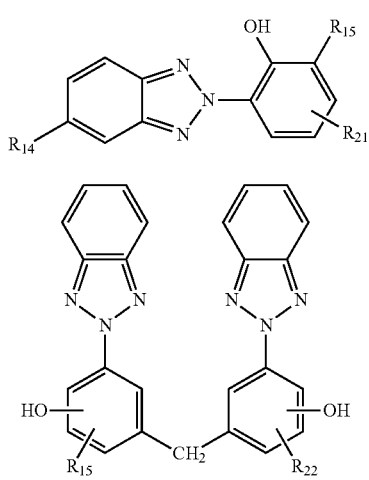

wherein $R_{14}$ is an optional $C_1$-$C_{18}$ alkyl or hydrogen; $R_{15}$ and $R_{22}$, independently, are optionally $C_1$-$C_{18}$ alkyl that may be substituted with a phenyl group, and $R_{21}$ is an optional functional group such as a $C_1$-$C_8$ alkyl that may include an ester linkage containing a methyl group. The UV-absorbing triazoles may be linked to the independent polyester moieties.

The polyester moieties may each include or consist of n repeat units such as (IV) or (V) below:

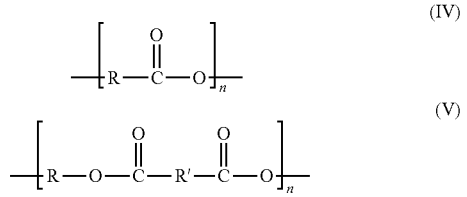

In structures (IV) and (V): R and R' represent hydrocarbons such as alkyl, aryl, or aralkyl chains (saturated or unsaturated) having a carbon chain length ranging independently from $C_1$-$C_{100}$, such as $C_4$-$C_{50}$, such as $C_6$-$C_{40}$; n is the degree of polymerization of each of the independent polyester moieties and may range from 1 to about 20, such as from 1 to about 10, such as from 1 to about 5. The total degree of polymerization, i.e., the sum of n for all polyester moieties in the UV-absorbing polyester, may range from 4 to about 25, such as from about 5 to about 20, such as from 5 to about 10.

According to certain embodiments, the UV-absorbing polyester has a weight average molecular weight (Mw) of about 2,000 or more, such as about 4,000 or more, such as from about 4,000 to about 4,500, as determined by gel permeation chromatography using, for example, the following conditions and detection system.

Determination of Mw may be performed using the following gel permeation chromatography (GPC) method and equipment. A suitable liquid chromatography system is an Agilent 1100/1200 Series high performance liquid chromatography system, the hardware of the which includes 5 modules; a G1379A degasser, a Model G1310A isocratic pump, a 1110 automatic liquid sampler Model G1313A, a Model G1316A thermostatted column compartment, and a Model G1362A refractive index detector (RID). The system is controlled using Agilent LC Chemstation software, Revision B.03.02. The system is fitted with two Varian MesoPore GPC Columns, 300×7.5 mm, 3 um, multipore. The samples are dissolved in ACS HPLC grade tetrahydrofuran (THF) to a concentration of approximately 1.0 mg/ml. The THF contains 250 ppm butylated hydroxytoluene (BHT) as oxidation inhibitor. The THF is filtered using 0.45 um Millipore filter before being used as the mobile phase solvent and dissolution solvent. The solvent is degassed continuously by the vacuum degasser in the system. The mobile phase flow rate is 1 mL/min. The two column set is held at 45° C. in the column compartment. The injection volume is 200 microliters. The run time is thirty minutes.

Calibration of the GPC column is performed using 10 narrow molecular weight distribution polystyrene standards with molecular weights of 162, 580, 1110, 1530, 2340, 3790, 5120, 7210, 12830, and 19640 Daltons, respectively. The standards may be purchased from Agilent-Varian. Each standard is injected and the molar mass is linearly regressed against elution volume to give the calibration line. Molecular weight calculations for the polyesters are determined using Agilent GPC Addon Revision B.01.01, an add-on to Agilent Chemstation software. All results for inventive polyesters given in the units of Daltons, are relative to the polystyrene standards.

In certain embodiments, in order to enhance water-resistance and spreadability, the UV-absorbing polyester may have a low water-solubility. By "water-solubility" it is meant the maximum weight percentage of polyester (relative to polyester plus water) that can be placed into 100 grams deionized water and agitated so that a clear solution is obtained and remains visually homogeneous and transparent at ambient temperature for 24 hours. For example, in certain embodiments, the UV-absorbing polyester may have a water-solubility that is about 3% or less, such as about 1% or less.

The UV-absorbing polyesters suitable for use in compositions of the present invention may be synthesized by various means known to those skilled in the art, e.g., ring opening of a lactone (cyclic ester) that bears a UV-absorbing moiety; a condensation reaction of a UV-absorbing monomer having both acid and alcohol functionality (e.g., an "A-B" condensation reaction); condensing a polyol functional monomer and a polyacid functional monomer, one or both of which includes UV-absorbing moieties; and the like.

One particularly suitable process for making the UV-absorbing polyester is via a transesterification reaction, such as by reacting a polyfunctional hydroxyl, e.g., a tetrol polyol (a molecule having four alcohol functional groups), a diol, a di-carboxylic acid, and an ester-functional UV-absorbing monomer. For example, three monomers, each absent a UV-absorbing moiety, e.g., a diol, a tetrol polyol and a di-carboxylic acid, may be reacted with a fourth monomer, e.g., a UV-absorbing triazole having an ester functionality, to produce a UV-absorbing polyester. The mole ratio of monomers may be selected such that the ratio of various monomer pairs is from about 0.25:1 to about 4:1. According to one embodiment, the mole fraction of UV-absorbing monomer, e.g., UV-absorbing triazole, relative to the total number of moles of all monomers used in the reaction (including the UV-absorbing monomer) is selected to be about 0.39 to about 0.60, or about 0.37 to about 0.42. According to another embodiment, this mole fraction is selected to be about 0.45 or less.

One particularly suitable UV-absorbing polyester is formed by a transesterification reaction of the following monomers: (1) dimerdiol, $C_{36}H_{72}O_2$, CAS No. 147853-32-5, which is a $C_{36}$ diol; (2) di-trimethylolpropane, $C_{12}H_{26}O_5$, CAS No. 23235-61-2, which is a tetrafunctional alcohol (tetrol polyol) derived from the dimerization of trimethylolpropane; (3) dimethyladipate, $C_8H_{14}O_4$, CAS No 627-93-0, the methyl ester of adipic acid; and (4) benzenepropanoic acid, 3-(2h-benzotriazol-2-yl)-5-(1,1-dimethylethyl)-4-hydroxy-, methylester, $C_{20}H_{23}N_3O_3$, CAS No 84268-33-7, a UV-absorbing monomer (includes a UV-absorbing triazole). Dimerdiols are described in United States patent, U.S. Pat. No. 7,427,640.

According to certain embodiments, the sunscreen agent consists of, or consists essentially of, the UV-absorbing polyester, as defined herein. According to certain other embodiments, the sunscreen agent may include additional UV-absorbing polymers, other than those UV-absorbing polyesters, as defined herein, and/or non-UV-absorbing, light-scattering particles. Additional UV-absorbing polymers are molecules that can be represented as having one or more structural units that repeat periodically, e.g., at least twice, to generate the molecule, and may be UV-absorbing polyesters, other than those as defined and claimed in this specification.

Additional UV-absorbing polymers may have a molecular weight of greater than about 1500. Examples of suitable additional UV-absorbing polymers include benzylidene malonate silicone, including those described in U.S. Pat. No. 6,193,959, to Bernasconi et al. A particularly suitable benzylidene malonate includes "Parsol SLX," commercially available from DSM (Royal DSM N.V.) of Heerlen, Netherlands. Other suitable additional UV-absorbing polymers are disclosed in U.S. Pat. No. 6,962,692; U.S. Pat. No. 6,899,866; and/or U.S. Pat. No. 6,800,274; including hexanedioic acid, polymer with 2,2-dimethyl-1,3-propanediol, 3-[(2-cyano-1-oxo-3,3-diphenyl-2-propenyl)oxy]-2,2-dimethylpropyl 2-octyldodecyl ester; sold under the trade name "POLYCRYLENE," commercially available from the HallStar Company of Chicago, Ill. When utilized, such additional UV-absorbing polymers may be used at concentrations of about 1% or more, for example about 3% or more.

Non-UV-absorbing, light-scattering particles do not absorb in the UV spectrum, but may enhance SPF by scattering of the incident UV radiation. Examples of non-UV-absorbing, light-scattering particles include solid particles having a dimension, e.g., average diameter, from about 0.1 micron to about 10 microns. In certain embodiments, the non-UV-absorbing, light-scattering particle is a hollow particle comprising, or consisting essentially of, an organic polymer or a glass. Suitable organic polymers include acrylic polymers, including acrylic/styrene copolymers, such as those known as SUNSPHERES, which are commercially available from Dow Chemical of Midland, Mich. Suitable glasses include borosilicate glasses such as those described in published United States Patent Application US20050036961A1, entitled, "AESTHETICALLY AND SPF IMPROVED UV-SUNSCREENS COMPRISING GLASS MICROSPHERES".

Topical Composition

In one embodiment, a composition suitable for topical/cosmetic use for application to the human body (e.g., keratinaceous surfaces such as the skin, hair, lips, or nails), especially the skin, is provided. The composition includes one or more UV-absorbing polyester(s) described herein. As discussed above, the concentration of the UV-absorbing polyester is sufficient to provide an SPF of about 10 or greater, particularly in the absence or substantial absence of other UV-absorbing polymers or non-polymeric UV-absorbing sunscreen agents as described herein. Accordingly, the concentration of the UV-absorbing polyester may vary from about 5% to about 50% by weight, such as from about 7% to about 40% of the composition, such as from about 10% to about 25% of the composition. In certain embodiments the concentration of UV-absorbing polymer is about 10% or more, such as about 15% or more, such as about 25% or more of the composition. According to certain embodiments where the sunscreen agent consists essentially of the UV-absorbing polyester, the concentration of the UV-absorbing polyester may be about 15% or more.

The concentration of non-UV-absorbing sunscreen agents, if present, may be about 1% or more, such as from about 1% to about 10%, such as from about 2% to about 5%. In certain embodiments where the UV-sunscreen agent further includes a non-UV-absorbing sunscreen agent in amounts as discussed above, compositions of the present invention may have an SPF of about 20 or greater.

Compositions of the present invention are substantially free of non-polymeric UV-absorbing sunscreen agents. By "substantially free of non-polymeric UV-absorbing sunscreen agents," it is meant that the compositions do not contain non-polymeric UV-absorbing sunscreen agents in an amount effective to provide the compositions with an SPF of greater than 2 in the absence of the UV-absorbing polyesters, as determined via the in vitro method described herein below. For example, the compositions of the invention will contain about 1% or less, or about 0.5% or less, of such non-polymeric UV-absorbing sunscreen agents. The compositions will have an SPF of less than 2 in the absence of the UV-absorbing polyester. One example of non-polymeric UV-absorbing sunscreen agents that the composition is substantially free of typically may be characterized as "organic" (include predominantly or only atoms selected from carbon, hydrogen, oxygen, and nitrogen) and having no definable repeat unit and typically having molecular weights that are about 600 daltons or less, such as about 500 daltons or less, such as less than 400 daltons. Examples of such compounds, sometimes referred to as "monomeric, organic UV-absorbers" include, but are not limited to: methoxycinnamate derivatives such as octyl methoxycinnamate and isoamyl methoxycinnamate; camphor derivatives such as 4-methyl benzylidene camphor, camphor benzalkonium methosulfate, and terephthalylidene dicamphor sulfonic acid; salicylate derivatives such as octyl salicylate, trolamine salicylate, and homosalate; sulfonic acid derivatives such as phenylbenzimidazole sulfonic acid; benzone derivatives such as dioxybenzone, sulisobenzone, and oxybenzone; benzoic acid derivatives such as aminobenzoic acid and octyldimethyl para-amino benzoic acid; octocrylene and other β,β-diphenylacrylates; dioctyl butamido triazone; octyl triazone; butyl methoxydibenzoyl methane; drometrizole trisiloxane; and menthyl anthranilate.

Other non-polymeric UV-absorbing sunscreen agents that the composition is substantially free of may include ultraviolet-absorbing particles, such as certain inorganic oxides, including titanium dioxide, zinc oxide, and certain other transition metal oxides. Such ultraviolet screening particles are typically solid particles having a diameter from about 0.1 micron to about 10 microns.

The compositions of the present invention may be used for a variety of cosmetic uses, especially for protection of the skin from UV radiation. The compositions, thus, may be made into a wide variety of delivery forms. These forms include, but are not limited to, suspensions, dispersions, solutions, or coatings on water soluble or water-insoluble substrates (e.g., substrates such as organic or inorganic powders, fibers, or films). Suitable product forms include lotions, creams, gels, sticks, sprays, ointments, mousses, and compacts/powders. The composition may be employed for various end-uses, such as recreation or daily-use sunscreens, moisturizers, cosmetics/make-up, cleansers/toners, anti-aging products, or combinations thereof. The compositions of the present invention may be prepared using methodology that is well known by an artisan of ordinary skill in the field of cosmetics formulation.

Compositions of the present invention include a continuous water phase in which a discontinuous oil phase that includes the UV-absorbing polyester is substantially homogeneously distributed. In certain embodiments, the UV-absorbing polyester is dissolved, as opposed to being dispersed or suspended, within the oil phase. The oil phase may, in turn, be stabilized within the water phase. The oil phase may be such that it is present in discrete droplets or units having an average diameter of about one micron to about 1000 microns, such as from about 1 micron to about 100 microns.

The relative concentrations of water phase and oil phase may be varied. In certain embodiments the percentage by weight of water phase is from about 10% to about 90%, such as from about 40% to about 80%, such as from 50% to about 80%; wherein the balance is oil phase.

The percentage of water included in the compositions may range from about 20% to about 90%, such as from about 20% to about 80%, such as from about 30% to about 70%, such as from about 51% to about 80%, such as from about 51% to about 70%, such as from about 51% to about 60%.

Topical Carrier

The one or more UV-absorbing polyesters in the composition may be combined with a "cosmetically-acceptable topical carrier," i.e., a carrier for topical use that is capable of having the other ingredients dispersed or dissolved therein, and possessing acceptable properties rendering it safe to use topically. As such, the composition may further include any of various functional ingredients known in the field of cosmetic chemistry, for example, emollients (including oils and waxes) as well as other ingredients commonly used in personal care compositions, such as humectants, thickeners, opacifiers, fragrances, dyes, solvents for the UV-absorbing polyester, among other functional ingredients. Suitable examples of solvents for the UV-absorbing polyester include dicaprylyl carbonate available as CETIOL CC from Cognis Corporation of Ambler, Pa. In order to provide pleasant aesthetics, in certain embodiments of the invention, the composition is essentially free of volatile solvents; in particular, $C_1$-$C_4$ alcohols such as ethanol and isopropanol.

Furthermore, the composition may be essentially free of ingredients that would render the composition unsuitable for topical use. As such, the composition may be essentially free of solvents such as volatile solvents, and, in particular, free of volatile organic solvents such as ketones, xylene, toluene, and the like.

Film-Forming Polymer

Compositions of the present invention include a film forming polymer. The film-forming polymer may, when dissolved, emulsified, or dispersed in one or more diluents, permit a continuous or semi-continuous film to be formed when it is spread with a liquid vehicle onto a smooth substrate such as glass, and the liquid vehicle is allowed to evaporate. As such, the polymer may dry on the glass in a manner in which over the area which it is spread should be predominantly continuous, rather than forming a plurality of discrete, island-like structures. The films formed by applying compositions on the skin according to embodiments of the invention described herein, may be less than, on average, about 100 microns in thickness, such as less than about 50 microns.

In contrast to polymeric UV-absorbing polymers, film-forming polymers generally do not absorb appreciable ultraviolet radiation and therefore do not meet the requirements for UV-absorbing polymers. However, by improving film formation, film-forming polymers may enhance the UV-protection (UV-A, UV-B or both) of the composition and/or enhance the waterproofing or water resistance of the composition.

The film-forming polymer is an alkylated polyvinylpyrrolidone, such as a copolymer of vinylpyrrolidone and an α-olefin, such as a copolymer of vinylpyrrolidone and a long-chain (e.g., $C_{16}$ to $C_{30}$ α-olefin, e.g., GANEX V220, GANEX V216, GANEX WP660). In one particularly notable embodiment, the film-forming polymer is formed from 20% vinyl pyrrolidone and 80% C16 olefin (1-hexadecene), such as GANEX V216. GANEX film-forming polymers are commercially available from ISP Specialty Chemicals (now Ashland Specialty Ingredients) of Wayne, N.J.

Compositions of the present invention may include additional film-forming polymers, including natural polymers such as polysaccharides or proteins and synthetic polymers such as polyesters, polyacrylics, polyurethanes, vinyl polymers, polysulfonates, polyureas, polyoxazolines, and the like. Specific examples of additional film-forming polymers include, for example, hydrogenated dimer dilinoleyl/dimethylcarbonate copolymer, available from Cognis Corporation of Ambler, Pa. as COSMEDIA DC; and water-dispersible polyesters, including sulfopolyesters such those commercially available from Eastman Chemical as EASTMAN AQ 38S.

The amount of film-forming polymer present in the composition may be from about 0.1% to about 5%, or from about 0.3% to about 3%, or from about 1% to about 2.5%.

Oil-in Water Emulsifier

Compositions of the present invention include one or more oil-in-water (O/W) emulsifiers selected from a group consisting of anionic emulsifiers and non-ionic emulsifiers. By "emulsifier," it is meant any of a variety of molecules that are suitable for emulsifying discrete oil-phase droplets in a continuous water phase. By "low molecular weight emulsifiers," it is meant emulsifiers having a molecular weight of about 2000 daltons or less, such as about 1000 daltons or less. The O/W emulsifier may be capable of lowering the surface tension of pure deionized water to 45 dynes per centimeter when added to pure deionized water at a concentration of O/W emulsifier of 0.5% or less at room temperature. The O/W emulsifier may have a hydrophile-lipophile balance (HLB) that is about 8 or more, such as about 10 or more.

In certain embodiments, the composition includes one or more anionic emulsifiers. Examples of suitable chemical classes of anionic emulsifiers are alkyl, aryl or alkylaryl, or acyl-modified versions of the following moieties: sulfates, ether sulfates, monoglyceryl ether sulfates, sulfonates, sulfosuccinates, ether sulfosuccinates, sulfosuccinamates, amidosulfosuccinates, carboxylates, amidoethercarboxylates, succinates, sarcosinates, amino acids, taurates, sulfoacetates, and phosphates. Notable anionic emulsifiers are salts of esters of phosphoric acid and cetyl alcohol, such as potassium salts of mixtures of esters of phosphoric acid and cetyl alcohol (e.g., 1-hexadecanol, dihydrogen phosphate, monopotassium salt). One notable example is potassium cetyl phosphate, hydrogenated palm glycerides, available as EMULSIPHOS from Symrise of Holzminden, Germany.

In certain embodiments, the concentration of the one or more anionic emulsifiers is from about 0.5% to about 6%, such as from about 1% to about 4%, such as from about 1% to about 2.5%.

In another embodiment of the invention, the composition includes one or more non-ionic emulsifiers. Examples of non-ionic emulsifiers include fatty amides, monoglycerides; sorbitan esters; polyoxyethylene derivatives of polyol esters; alkyl glucosides or polyglucosides; polyglyceryl esters; non-crosslinked silicone copolymers such as alkoxy or alkyl dimethicone copolyols, silicones having pendant hydrophilic moieties such as linear silicones having pendant polyether groups or polyglycerin groups; crosslinked elastomeric solid organopolysiloxanes comprising at least one hydrophilic moieties: polyethylene glycol, polypropylene glycol or polyglyceryl esters. According to one embodiment the non-ionic emulsifier has no alcohol functional groups. According to one embodiment of the invention, the non-ionic emulsifier has a molecular weight of about 10,000 daltons or less, such as about 7000 daltons or less.

According to one embodiment, the non-ionic surfactant is an ester of a fatty acid, such as various saturated or unsaturated, linear or branched, $C_7$-$C_{22}$ unethoxylated, aliphatic acids. The fatty acid may have from 14 to about 22 carbon atoms, such as from about 16 to about 18 carbon atoms. According to one embodiment, the non-ionic emulsifier is a polyether, such as selected from a fatty acid ester of glycerol (such as glyceryl stearate), a polyethylene glycol fatty acid ester (such as PEG-100 Stearate), and combinations thereof.

Specifically excluded from non-ionic surfactants are oil-gelling polymers, such as polymers that are capable of forming a gel with mineral oil at 25° C., such as when the oil-gelling polymer is mixed with mineral oil to a concentration of oil-gelling polymer that is between about of 0.25% to 2.0% by weight, the resulting mixture having a yield stress of about 5 pascals (Pa) or more, such as about 10 Pa or more, such as from about 10 Pa to about 1100 Pa. Examples of oil-gelling polymers are $C_2$-$C_4$ alkylcellulose polymers, such as ethylcellulose, which is an ethyl ether of cellulose comprising a long-chain polymer consisting of anhydroglucose units joined together by acetal linkages. Other examples of oil-gelling polymers are dibutyl ethylhexanoyl glutamide and dibutyl lauroyl glutamide.

The concentration of non-ionic emulsifer may also range from about 1% to about 10%, such as from about 2% to about 6%, such as from about 2% to about 4%.

In certain embodiments, in addition to the emulsifier(s) discussed above, the composition includes an additional emulsifier such as one or more of an amphoteric emulsifier, a cationic emulsifier, and/or a polymeric emulsifier. Examples of suitable chemical classes of amphoteric emulsifier include alkyl betaines, amidoalkyl betaines, alkylamphoacetates; amidoalkyl sultaines; amphophosphates; phosphorylated imidazolines; carboxyalkyl alkyl polyamines; alkylimino-dipropionates; alkylamphoglycinates (mono or di); alkylamphoproprionates; N-alkyl β-aminoproprionic acids; and alkylpolyamino carboxylates. Examples of suitable chemical classes of cationic emulsifier include alkyl quaternaries, benzyl quaternaries, ester quaternaries, ethoxylated quaternaries, and alkyl amines Examples of suitable chemical classes of polymeric emulsifiers include copolymers based on acrylamidoalkyl sulfonic acid such as Aristoflex® AVC and Aristoflex® HMB by Clariant Corporation; and Granthix APP by Grant Industries, Inc.

In certain embodiments, the composition includes an emollient used for the prevention or relief of dryness and for the protection of the skin, as well as solubilizing the UV-absorbing polyester. Suitable emollients include mineral oils, petrolatum, vegetable oils (e.g. triglycerides such as caprylic/capric triglyceride), waxes and other mixtures of fatty esters, including but not limited to esters of glycerol (e.g, isopropyl palmitate, isopropyl myristate), and silicone oils such as dimethicone. In certain embodiments, mixtures of triglycerides (e.g. caprylic/capric triclycerides) and esters of glycols (e.g. isopropyl myristate) may be used to solubilize the UV-absorbing polyesters.

In certain embodiments, the composition includes a pigment suitable for providing color or hiding power. The pigment may be one suitable for use in a color cosmetic product, including compositions for application to the hair, nails and/or skin, especially the face. Color cosmetic compositions include, but are not limited to, foundations, concealers, primers, blush, mascara, eyeshadow, eyeliner, lipstick, nail polish and tinted moisturizers.

The pigment suitable for providing color or hiding power may be composed of iron oxides, including red and yellow iron oxides, titanium dioxide, ultramarine and chromium or chromium hydroxide colors, and mixtures thereof. The pigment may be a lake pigment, e.g., an organic dye such as azo, indigoid, triphenylmethane, anthraquinone, and xanthine dyes that are designated as D&C and FD&C blues, browns, greens, oranges, reds, yellows, etc., precipitated onto inert binders such as insoluble salts. Examples of lake pigments include Red #6, Red #7, Yellow #5 and Blue #1. The pigment may be an interference pigment. Examples of interference pigments include those containing mica substrates, bismuth oxycloride substrates, and silica substrates, for instance mica/bismuth oxychloride/iron oxide pigments commercially available as CHROMALITE pigments (BASF), titanium dioxide and/or iron oxides coated onto mica such as commercially available FLAMENCO pigments (BASF), mica/titanium dioxide/iron oxide pigments including commercially available KTZ pigments (Kobo products), CELLINI pearl pigments (BASF), and borosilicate-containing pigments such as REFLECKS pigments (BASF).

The compositions of the present invention may further comprise one or more other cosmetically active agent(s). A "cosmetically active agent" is a compound that has a cosmetic or therapeutic effect on the skin, e.g., agents to treat wrinkles, acne, or to lighten the skin. The cosmetically active agent will typically be present in the composition of the invention in an amount of from about 0.001% to about 20% by weight of the composition, e.g., about 0.01% to about 10% such as about 0.1% to about 5% by weight of the composition.

In certain embodiments the composition has a pH that is from about 4.0 to about 8.0, such as from about 5.5 to about 7.0.

Water resistance may be measured using, for example, the In-Vitro Water Resistance Test, as set forth below. A higher water resistance value of a composition tends to indicate more resistance of films of the composition to being removed by water, as compared to a composition having a lower water resistance value, which compositions tends to indicate less resistance of films of the composition to being removed by water. Applicants have recognized that the compositions of the present invention have surprisingly high water resistance values associated therewith. For example, in certain embodiments, the compositions have a Water Resistance Value (WRV) of about 65% or greater. In certain other embodiments, the compositions exhibit a WRV of about 80% or greater, such as about 90% or greater.

The compositions of the present invention may be prepared using mixing and blending methodology that is well known by an artisan of ordinary skill. In one embodiment of the invention, a method of making a composition of the present invention includes preparing an oil phase by mixing at least the UV-absorbing polyester with optional oil-soluble or oil-miscible ingredients; and preparing a water phase, by mixing water and optional water-soluble or water-miscible ingredients. The oil phase and the water phase may then be mixed in a manner sufficient to disperse the oil phase substantially homogeneously in the water phase such that the water phase is continuous and the oil phase discontinuous.

The compositions of the present invention can be used by topically administering to a mammal, e.g., by the direct laying on, wiping or spreading of the composition on the skin or hair of a human.

The following Water Resistance Test is used in the instant methods and in the following Examples.

Water-Resistance Test:

The potential for water resistance of a given formulation is measured in accordance with the Water Resistance Test as set forth below. A WRV of greater than 65% is considered to be particularly high, while a WRV of greater than 80% is even more desirable, and a WRV of greater than 90% is even more desirable.

The Water Resistance Test is conducted in the following manner. For each sample, the product is applied to PMMA plates and the initial SPF is measured according to the procedure, IN-VITRO SPF METHOD, described below. Initial SPF is measured with the labsphere instrumentation immediately following the 15 minute drying period, then a single sunscreen coated PMMA plate is attached to an 18 inch rod containing 4 propeller type mixing blades. The mixing rod+plate are immersed into a 3 L beaker of deionized water. The mixing blade is rotated at 35 rpm for exactly 20 minutes. The plate is removed from the water after 20 minutes and is allowed to air dry for 2 hours. The final SPF is read on the dry plate. The WRV is calculated by dividing the final SPF by the initial SPF and multiplying by 100. A fresh 3 L of deionized water is used for each plate.

Sun protection factor (SPF) may be tested using the following IN-VITRO SPF TEST METHOD. The baseline transmission of a PMMA plate (substrate) without application of any test materials applied thereto was measured. Test samples were prepared by providing a sample of polymer. Blends may also be tested by this method. The polyester(s) can be tested without any additional additives; with a solvent system, or as a part of a personal care composition that may include solvent and/or additional ingredients.

Each sample is separately applied to a PMMA plate (available from Helioscience, Marseille, France) using an application density of 2 micro liters of solution per square centimeter of substrate, rubbing it into a uniform thin layer with the operator's finger, and allowing to dry. The samples are allowed to dry for 15 minutes before measurement of absorbance using calibrated Labsphere® UV-1000S UV transmission analyzer (Labsphere, North Sutton, N.H., USA). The absorbance measures were used to calculate SPF and PFA indices (biological protection factor in the UVA based).

SPF and PFA may be calculated using methods known in the art—see equation (1) below for calculation of SPF:

$$SPF_{in\ vitro} = \frac{\int_{\lambda=290\ nm}^{\lambda=400\ nm} E(\lambda)*I(\lambda)*d\lambda}{\int_{\lambda=290\ nm}^{\lambda=400\ nm} E(\lambda)*I(\lambda)*10^{-A_0(\lambda)}*d\lambda} \quad (1)$$

where:
$E(\lambda)$=Erythema action spectrum
$I(\lambda)$=Spectral irradiance received from the UV source
$A0(\lambda)$=Mean monochromatic absorbance of the test product layer before UV exposure
$d\lambda$=Wavelength step (1 nm)

EXAMPLES

The following examples illustrate the preparation and efficacy of compositions of the present invention.

Example I

The following example illustrates the high water resistance of certain compositions of the present invention. Inventive compositions (E1-E3) include UV-absorbing polyesters, are substantially free of UV-screening compounds and further include an alkylated polyvinylpyrrolidone, as well as an anionic or non-ionic emulsifier. These inventive examples were prepared as shown in Table 1 and described below.

Inventive Example E1 was made by the following process: A water phase was prepared by adding water to a main vessel and heating to 70° C.-75° C. with mixing. PEMULEN TR-2 was added and mixed until dissolved. EUXYL PE9010 was added and mixed until dissolved. An oil phase was prepared by charging a vessel with CETIOL CC and mixing. At 60° C. the UV-absorbing polyester was added to the vessel. ARLACEL 165 and GANEX 216 were added to the oil phase and the mixture was heated to about 80° C. under continuous mixing, until uniform. The heated oil phase was added to the water phase with moderate shear. Moderate mixing was continued during cooling. At about 40° C., silica was gently added to the formulation.

Inventive Example E2 was made by the following process. A water phase was prepared by adding water to a main vessel and heating to 75° C.-80° C. with mixing. EUXYL PE9010 was added to the water phase. An oil phase was prepared by charging a vessel with CETIOL CC and mixing. At 60° C. the UV-absorbing polyester was added. ARLACEL 165 and GANEX 216 were added to the oil phase and the mixture was heated to about 75° C.-80° C. under continuous mixing, until uniform. The heated oil phase was added to the water phase with moderate shear. Moderate mixing was continued during cooling. At about 40° C., silica and Cosmedia ATH were gently added to the formulation.

Inventive Example E3 was made by the following process. A water phase was prepared by adding water to a main vessel and heating to 75° C.-80° C. with mixing. An oil phase was prepared by charging a vessel with CETIOL CC and mixing. At 60° C. the UV-absorbing polymer was added.

EMULSIPHOS, CRODACOL C95, and GANEX 216 were added, and mixture was heated to about 75-80° C. under mixing. The hot oil phase was added to the water phase with moderate shear. Moderate mixing was continued during cooling. At about 40 C, silica was gently added to the formulation. Subsequently, EUXYL PE 9010 was mixed into the formulation.

TABLE 1

Inventive Examples

| | E1 | E2 | E3 |
|---|---|---|---|
| $H_2O$ | 66.7 | 66 | 64.5 |
| Pemulen TR2 | 0.3 | | |
| CETIOL CC Dicapryl Carbonate | 10 | 10 | 10 |
| UV-Absorbing Polyester (80% solution in dicaprylyl carbonate) | 15 | 15 | 15 |
| ARLACEL 165 veg Glyceryl Stearate (and) PEG-100 Stearate | 2 | 2 | |
| Ganex V216 | 2 | 2 | 2 |
| Emulsiphos | | | 2 |
| CRODACOL C95 | | | 2.5 |
| Cetyl Alcohol | | | |
| Silica | 3 | | |
| Silica (Silispheres) | | 3 | 3 |
| Euxyl PE 9010 | 1 | 1 | 1 |
| Cosmedia ATH | | | 1 |

PEMULEN TR-2 is Acrylates/$C_{10-30}$ Alkyl Acrylate Crosspolymer, available from Noveon/Lubrizol of Wickliffe, Ohio. CETIOL CC is Dicaprylyl Carbonate, available from Cognis, now BASF of Ludwigshafen, Germany. EUXYL PE 9010 is phenoxyethanol and ethylhexyl glycerin, available from Tri-K Industries of Northvale, New Jersey. GANEX V-216 is copolymer of vinylpyrrolidone and a $C_{16}$ α-olefin, available from ISP Specialty Chemicals (now Ashland Specialty Ingredients) of Wayne, New Jersey. ARLACEL 165 veg is Glyceryl Stearate (and) PEG-100 Stearate, available from Croda of Edison, New Jersey. CRODACOL C95 is a range of saturated fatty alcohols, available from Croda PLC of Edison, New Jersey. EMULSIPHOS is Potassium Cetyl Phosphate and Hydrogenated Palm Glycerides, available from Symrise of Holzminden, Germany.

The UV-absorbing polyester was prepared from the following four monomers: (1) dimerdiol, $C_{36}H_{72}O_2$, CAS No. 147853-32-5 (referred to as "DDO" in Table 1, below); (2) di-trimethylolpropane, $C_{12}H_{26}O_5$, CAS No. 23235-61-2 ("DITMP"); (3) dimethyladipate, $C_8H_{14}O_4$, CAS No 627-93-0 ("DMA"); and (4) benzenepropanoic acid, 3-(2h-benzotriazol-2-yl)-5-(1,1-dimethylethyl)-4-hydroxy-, methyl-ester, $C_{20}H_{23}N_3O_3$, CAS No 84268-33-7 ("triazole"). The mole ratio of the four monomers (DDO:DITMP:DMA:TRIAZOLE was: 3.4:2.1:4.0:6.0. Therefore, the UV-absorbing polyester had a mole fraction of UV-absorbing triazole of about 0.39. The weight average molecular weight was estimated to be about 4192. The resulting UV-absorbing polyester was combined with a sufficient amount of dicaprylyl carbonate (CETIOL CC) to form a UV-absorbing polyester solution that was 80% by weight UV-absorbing polyester and 20% by weight dicaprylyl carbonate.

In addition to the Inventive Examples E1-E3, Comparative Examples, C1-C5 were prepared as shown in Table 2 and described below.

TABLE 2

Comparative Examples, C1-C5

| | C1 | C2 | C3 | C5 |
|---|---|---|---|---|
| H20 | 62.7 | 57.7 | 69 | 63.8 |
| Xanthan Gum | | | 0.3 | |
| PEMULEN TR2 | 0.3 | 0.3 | | 0.2 |
| Dicapryl Carbonate | 10 | 10 | 10 | 10 |
| UV-Absorbing Polyester (80% solution in dicaprylyl carbonate) | 15 | 15 | 15 | 15 |
| Glyceral Stearate: PEG-100 Stearate | | | 1.7 | |
| GANEX 216 | | 2 | | |
| EMULFREE CBG | 6 | 6 | | |
| EMULSIPHOS | | | | 2 |
| Cetyl Alcohol | 5 | 5 | | 5 |
| Silica | | | 3 | |
| Silica (Silispheres) | | 3 | | 3 |
| PHENONIP XB | 1 | | | |
| EUXYL PE 9010 | | 1 | 1 | 1 |

COSMEDIA ATH is a hydrogenated dimer dilinoleyl/dimethylcarbonate copolymer, available from Cognis Corporation of Ambler, Pennsylvania. EMULFREE CBG is a mixture of cocoate mono and di-esters of butylene glycol, isostearyl alcohol, and ethyl cellulose; available from Gattefosse of Paris, France
Other ingredients are as described in other portions of this specification.

Comparative Examples C1-C2 were made by the following process: A water phase was prepared by adding water to a main vessel and heating to 70° C.-75° C. with mixing. EUXYL PE9010 (C2) or PHENONIP XB (C1) was added and mixed until dissolved. PEMULEN was added slowly and mixed rapidly until uniform. The water phase was partially neutralized before emulsification. An oil phase was prepared by charging a vessel with CETIOL CC and mixing. CRODACOL C95 was added and heat was applied. At 60° C. the UV-absorbing polyester was added. EMULFREE CBG (C1) and EMULFREE plus GANEX 216 (C2), respectively, were added, and mixing was continued for 5 minutes and the mixture was heated to about 80° C. until uniform. The heated oil phase was added to the water phase with moderate shear. The pH was adjusted to 6.5 with sodium hydroxide, and moderate mixing was continued for 5 minutes. The mixture was allowed to slowly cool to room temperature at a reduced mixing speed.

Comparative Examples C3 and C4 were made by the following process: A water phase was prepared by adding water to a main vessel and heating to 75° C.-80° C. with mixing. Xanthan gum was added and mixed until dissolved. An oil phase was prepared by charging a vessel with CETIOL CC and mixing. At 60° C. the UV-absorbing polyester was added. ARLACEL 165 was added, and the mixture was heated to about 75° C.-80° C. under mixing, until uniform. The heated oil phase was added to the water phase with moderate shear. Moderate mixing was continued during cooling. At about 40° C., silica was gently added to the formulation. Subsequently, EUXYL PE 9010 was mixed into the formulation. Comparative Example C4 was identical to C3, except that 1% of COSMEDIA ATH was added at the end of the process.

Comparative Example C5 was made by the following process: A water phase was prepared by adding water to a main vessel and heating to 75° C.-80° C. with mixing. PEMULEN TR-2 was added and mixed until dissolved. An oil phase was prepared by charging a vessel with CETIOL CC and mixing. At 60° C. the UV-absorbing polyester was added. EMULSIPHOS and CRODACOL C95 were added, and the mixture was heated to about 75° C.-80° C. under mixing. The heated oil phase was added to the water phase with moderate shear. Moderate mixing was continued during cooling. At about 40 C, silica was gently added to the formulation. Subsequently, EUXYL PE 9010 was mixed into the formulation.

The WRVs of Inventive Examples E1-E3 and Comparative Example C1-C5 were determined using the Water Resistance Test as described above and the results reported in Table 3. The Water Resistance Tests were performed on three separate plates for all of the examples except C4 and C5, where testing was conducted only on a single PMMA plate.

TABLE 3

Water Resistance Testing

| Example | Description | WRV (mean) | Standard Deviation |
|---|---|---|---|
| Comparative Example, C1 | Oil-gelling polymer | 58.4 | 7.66 |
| Comparative Example, C2 | Oil-gelling polymer + alkylated polyvinylpyrrolidone | 58.5 | 17.3 |
| Inventive Example, E1 | Non-Ionic emulsifier + alkylated polyvinylpyrrolidone | 94.0 | 6.69 |
| Comparative Example, C3 | Non-Ionic emulsifier | 50.5 | 0.75 |
| Comparative Example, C4 | Non-Ionic emulsifier + dilinoleyl/dimethylcarbonate copolymer | 47.0 | — |
| Inventive Example, E2 | Non-Ionic emulsifier + alkylated polyvinylpyrrolidone + dilinoleyl/dimethylcarbonate copolymer | 90.4 | 22.6 |
| Comparative Example, C5 | Anionic emulsifier | 62.3 | |
| Inventive Example, E3 | Anionic emulsifier + alkylated polyvinylpyrrolidone | 97.8 | 14.6 |

The results of Water Resistance Test testing indicate that the addition of the alkylated polyvinylpyrrolidone film former (GANEX 216) significantly improved the water resistance of the compositions that included anionic or non-ionic emulsifiers. For example, the alkylated polyvinylpyrrolidone improved the water resistance of a composition with an anionic emulsifier, EMULSIFPHOS, as shown by comparing E3 and C5; or a composition with a non-ionic emulsifier, ARLACEL, as shown by comparing E1 and C3 or by comparing E2 and C4. However, the alkylated polyvinylpyrrolidone film former did not result in an increase in the water resistance of the compositions that did not include either of these types of emulsifier (Examples C1 and C2). Furthermore, using a film former with a hydrogenated dimer dilinoleyl/dimethylcarbonate copolymer (COSMEDIA ATH) without the alkylated polyvinylpyrrolidone did not improve water resistance, as shown by comparing C4 and C3.

Surprisingly, sunscreen compositions that include a UV-absorbing polyester and that are substantially free of, or are free of conventional non-polymeric UV-absorbing sunscreen agents only provide sufficient water resistance when specific emulsifiers (non-ionic and anionic) are used in combination with a film former.

It is understood that while the invention has been described in conjunction with the detailed description thereof, that the foregoing description is intended to illustrate and not limit the scope of the invention.

The invention claimed is:

1. A composition, comprising:
a continuous water phase,
a discontinuous oil phase homogeneously distributed in said water phase, said oil phase comprising a sunscreen agent comprising about 15% or more by weight of a UV-absorbing polyester, which UV-absorbing polyester is the polymerization reaction product of four monomers comprising (1) dimerdiol ("DDO"), $C_{36}H_{72}$, CAS No. 147853-32-5; (2) di-trimethylolpropane ("DITMP"), $C_{12}H_{26}O_5$, CAS No. 23235-61-2; (3) dimethyladipate ("DMA"), $C_8H_{14}O_4$, CAS No 627-93-0; and (4) benzenepropanoic acid, 3-(2h-benzotriazol-2-yl)-5-(1,1-dimethylethyl)-4-hydroxy-methylester ("triazole") $C_{20}H_{23}N_3O_3$, CAS No 84268-33-7, wherein the molar ratio of the four monomers (DDO:DITMP:DMA:triazole) is 3.4:2.1:4.0:6.0,
about 0.3 to about 3% by weight of an alkylated polyvinylpyrrolidone; and
an oil-in-water emulsifier selected from the group consisting of an anionic emulsifier and a non-ionic emulsifier, wherein, if said oil-in-water emulsifier comprises said anionic emulsifier, said anionic emulsifier is present at from about 0.5% to about 6% by weight, and wherein if said oil-in-water emulsifier comprises said non-ionic emulsifier, said non-ionic emulsifier is present at from about 1% to about 10% by weight and is free of an oil-gelling polymer; and
wherein said composition comprises less than 1% by weight of a non-polymeric UV-absorbing sunscreen agent, has an SPF of less than 2 in the absence of said UV-absorbing polyester, an SPF of about 20 or greater and a Water Resistance Value of greater than 65%.

2. The composition of claim 1 wherein said UV-absorbing polyester has a weight average molecular weight of about 4,000 or more.

3. The composition of claim 1 wherein the oil-in-water emulsifier is an anionic emulsifier.

4. The composition of claim 1 wherein the oil-in-water emulsifier is a non-ionic emulsifier.

5. The composition of claim 4 wherein the non-ionic emulsifier has a molecular weight of about 10,000 daltons or less.

6. The composition of claim 1 wherein the alkylated polyvinylpyrrolidone is present in a concentration by weight from about 1% to about 2.5%.

* * * * *